United States Patent
Metivier et al.

(10) Patent No.: US 6,245,936 B1
(45) Date of Patent: Jun. 12, 2001

(54) PROCESS FOR THE SELECTIVE PREPARATION OF A 2-HYDROXYBENZOIC ACID AND A 4-HYDROXYBENZALDEHYDE AND DERIVATIVES THEREOF

(75) Inventors: Pascal Metivier, Sainte Foy les Lyons; Christian Maliverney, Lyons; Philippe Denis, Decines, all of (FR)

(73) Assignee: Rhodia Chimie, Boulogne BillianCourt Cedex (FR)

( * ) Notice: Subject to any disclaimer, the term of this patent is extended or adjusted under 35 U.S.C. 154(b) by 0 days.

(21) Appl. No.: 09/284,378

(22) PCT Filed: Oct. 13, 1997

(86) PCT No.: PCT/FR97/01828

§ 371 Date: Apr. 12, 1999

§ 102(e) Date: Apr. 12, 1999

(87) PCT Pub. No.: WO98/16493

PCT Pub. Date: Apr. 23, 1998

(30) Foreign Application Priority Data

Oct. 14, 1996 (FR) .................................................. 96 12479

(51) Int. Cl.$^7$ ............................ C07C 51/16; C07C 45/29
(52) U.S. Cl. ......................... 562/418; 562/421; 562/407; 568/432
(58) Field of Search .................................. 562/421, 418, 562/407; 568/432

(56) References Cited

U.S. PATENT DOCUMENTS

| | | | |
|---|---|---|---|
| 3,673,257 | * 6/1972 | Di Bella | 260/600 |
| 4,192,959 | * 3/1980 | Bauer et al. | 568/764 |
| 4,351,962 | * 9/1982 | Gradeff et al. | 568/432 |
| 5,783,737 | * 7/1998 | Meltivier | 568/432 |

* cited by examiner

Primary Examiner—Rosalynd Keys
(74) Attorney, Agent, or Firm—Jean-Louis Seugnet

(57) ABSTRACT

The present invention concerns a process for the preparation of a 2-hydroxybenzoic acid and of a 4-hydroxybenzaldehyde and derivatives thereof from a mixture of two phenolic compounds, one carrying a formyl or hydroxymethyl group in the 2 position, and the other carrying a formyl or hydroxymethyl group in the 4 position. The invention also concerns the preparation of a 4-hydroxybenzaldehyde from said mixture. The invention more particularly concerns the preparation of 3-methoxy-4-hydroxybenzaldehyde and of 3-ethoxy4-hydroxybenzaldehyde, respectively known as "vanillin" and ethylvanillin". The process for the preparation of a 2-hydroxybenzoic acid and a 4-hydroxybenzaldehyde and derivatives thereof is characterised in that the formyl or hydroxymethyl group in the 2 position of compound (A) in a mixture of phenolic compounds, one (A) carrying a formyl or hydroxymethyl group in the 2 position, and the other (B) carrying a formyl or hydroxymethyl group in the 4 position, is selectively oxidised to a carboxy group and optionally a hydroxymethyl group of compound (B) in the 4 position is selectively oxidised to a formyl group, thus producing a mixture of a 2-hydroxybenzoic acid and a 4-hydroxybenzaldehyde.

43 Claims, No Drawings

PROCESS FOR THE SELECTIVE PREPARATION OF A 2-HYDROXYBENZOIC ACID AND A 4-HYDROXYBENZALDEHYDE AND DERIVATIVES THEREOF

This application is an application under 35 U.S.C. Section 371 of International Application Number PCT/FR97/01828, filed on Oct. 13, 1997.

The present invention concerns a process for the preparation of a 2-hydroxybenzoic acid and of a 4-hydroxybenzaldehyde and derivatives thereof from a mixture of two phenolic compounds, one carrying a formyl or hydroxymethyl group in the 2 position, and the other carrying a formyl or hydroxymethyl group in the 4 position.

The invention also concerns the preparation of a 4-hydroxybenzaldehyde from said mixture.

The invention more particularly concerns the preparation of 3-methoxy-4-hydroxybenzaldehyde and of 3-ethoxy-4-hydroxybenzaldehyde, respectively known as "vanillin" and ethylvanillin".

French patent application no. 95/06186 describes a process for the preparation of 4-hydroxybenzaldehydes, and more particularly of vanillin and of ethylvanillin.

The process described consists of preparing a 3-carboxy-4-hydroxybenzaldehyde, then of decarboxylation of said compound, thereby producing 4-hydroxybenzaldehyde.

3-carboxy-4-hydroxybenzaldehyde is prepared according to FR no. 95/06186 from one of the compounds, and mixtures thereof, having more particularly the following formulae (IIa), (IIb), (IIc) and (IId) shown below:

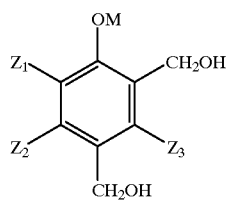
(IIa)

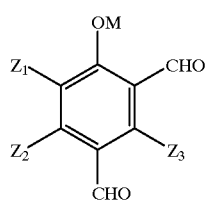
(IIb)

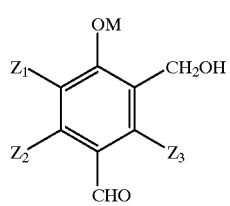
(IIc)

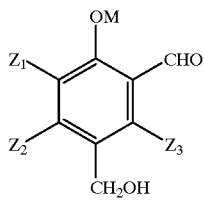
(IId)

where, in said formulae:

M represents a hydrogen atom and/or a metal cation from group (Ia) or (IIa), or an ammonium cation, $Z_1$, $Z_2$ and $Z_3$, which may be identical or different, represent a hydrogen atom, an alkyl, alkenyl, alkoxy, hydroxyalkyl, alkoxyalkyl, cycloalkyl, or aryl radical, a hydroxy group, a nitro group, a halogen atom, or a trifluoromethyl group.

The patented process starts with a bi-functional phenolic compound carrying on the aromatic ring two functional groups of the hydroxy group, which can be a —CHO group and/or a —CH$_2$OH group, at the ortho and para positions.

Firstly, the group in the ortho position is selectively oxidised to the carboxy group; the group in the para position being at the most oxidised to the formyl group. Thus, after eliminating the carboxy group in the ortho position, 4-hydroxybenzaldehyde is obtained.

Vanillin and ethylvanillin are advantageously obtained according to a selective process but one which is also highly competitive industrially as it uses less expensive reactants.

As a result of research, the applicant has found that it is possible a start with a mixture of monosubstituted phenolic compounds.

A process was found, and is object of the present invention, for the preparation of a 2-hydroxybenzoic acid and a 4-hydroxybenzaldehyde and derivatives thereof, which is characterised in that in a mixture of phenolic compounds, one (A) carrying a formyl or hydroxymethyl group in the 2 position, and the other (B) carrying a formyl or hydroxymethyl group in the 4 position, the formyl or hydroxymethyl group in the 2 position of compound (A) is selectively oxidised to a carboxy group and optionally a hydroxymethyl group of compound (B) in the 4 position is selectively oxidised to a formyl group, thus producing a mixture of a 2-hydroxybenzoic acid and a 4-hydroxybenzaldehyde.

In a successive step, the 4-hydroxybenzaldehyde is separated from the reaction medium.

A first variation of the invention consists of separating the 4-hydroxybenzaldehyde from the 2-hydroxybenzoic acid by pH controlled extraction of aldehyde.

Another variation of the invention consists of decarboxylation of only the 2-hydroxybenzoic acid in the mixture obtained, producing the initial phenolic compound which can then be recycled; the 4-hydroxybenzaldehyde is then recovered in a conventional manner.

According to the present invention, it was found that when starting with a mixture of phenolic molecules, one carrying hydroxymethyl or formyl groups in the ortho position of the hydroxyl group and the other carrying a hydroxymethyl or formyl group in the para position of the hydroxy group, oxidation to a carboxy group preferably takes place on the hydroxymethyl or formyl group carried by the (A) molecule, substituted in the ortho position.

The starting substrates used in the process are mixtures of phenolic compounds, one carrying a formyl or hydroxymethyl group in the 2 position and the other in the 4 position.

The term "phenolic compound" denotes any aromatic compound with an aromatic ring which carries a hydroxy group.

In the following description of the present invention, the term "aromatic" denotes the conventional idea of aromaticity as defined in the literature, particularly in "Advanced Organic Chemistry" by Jerry MARCH, 4th edition, John Wiley and Sons, 1992, pp. 40 ff.

Thus, a mixture (II) of phenolic compounds is used, more particularly with the following formulae:

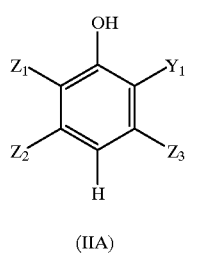 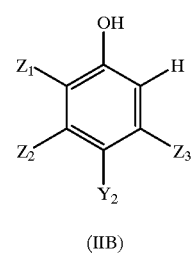

(IIA)      (IIB)

where, in said formulae (IIA) and IIB):

$Y_1$ and $Y_2$, which may be identical or different, represent one of the following groups:
  a —CHO group,
  a —CH$_2$OH group, $Z_1$, $Z_2$ and $Z_3$, which may be identical or different, represent a hydrogen atom, an alkyl, alkenyl, alkoxy, hydroxyalkyl, alkoxyalkyl, cycloalkyl, or aryl radical, a hydroxy group, a nitro group, a halogen atom, or a trifluoromethyl group.

Particularly suitable compounds for use in the process of the invention have formulae (IIA) and (IIB) where $Z_1$, $Z_2$ and $Z_3$, which may be identical or different, represent one of the following atoms or groups:
  a hydrogen atom,
  a linear or branched alkyl radical containing 1 to 12 carbon atoms, preferably 1 to 4 carbon atoms, such as methyl, ethyl, propyl, isopropyl, butyl, isobutyl, sec-butyl or tert-butyl,
  a linear or branch alkenyl radical containing 2 to 12 carbon atoms, preferably 2 to 4 carbon atoms, such as vinyl or allyl,
  a linear or branched alkoxy radical containing 1 to 12 carbon atoms, preferably 1 to 4 carbon atoms, such as a methoxy, ethoxy, propoxy, isopropoxy, butoxy, isobutoxy, sec-butoxy or tert-butoxy radical,
  a phenyl radical,
  a halogen atom, preferably a fluorine, chlorine or bromine atom.

The present invention does not exclude the presence on the aromatic cycle of substituents of a different nature, provided that they do not interfere with the reactions taking place in the process of the invention.

The present invention is preferably applicable to compounds with the formulae (IIA) and (IIB) where $Z_1$, represents a hydrogen atom or a linear or branched alkyl or alkoxy radical containing 1 to 6 carbon atoms, preferably 1 to 4 carbon atoms; $Z_2$ and $Z_3$ represent a hydrogen atom; and $Y_1$ and $Y_2$ are identical and represent a formyl group or a hydroxymethyl group.

Examples of preferred mixtures of phenolic compounds which can be used in the process of the invention are, inter alia:
  o-hydroxymethylphenol and p-hydroxymethylphenol,
  o-hydroxymethylguaiacol and p-hydroxymethylguaiacol,
  o-formylguaiacol and p-formylguaiacol,
  o-hydroxymethylguetol and p-hydroxymethylguetol,
  o-formylguetol and p-formylguetol.

According to the process of the invention, a mixture of phenolic compounds having preferably formula (II) is used as the starting compound.

The proportion of each hydroxymethylated or formylated phenolic compound in the mixture depends on how they are prepared.

By way of an example, the proportion of each isomer can vary greatly, for example from 10 to 90% by weight, and more preferably between 30 and 70%.

The reaction scheme of the process according to the invention is given below to facilitate comprehension of the disclosure of the invention, without in any way binding the scope of the invention to said scheme.

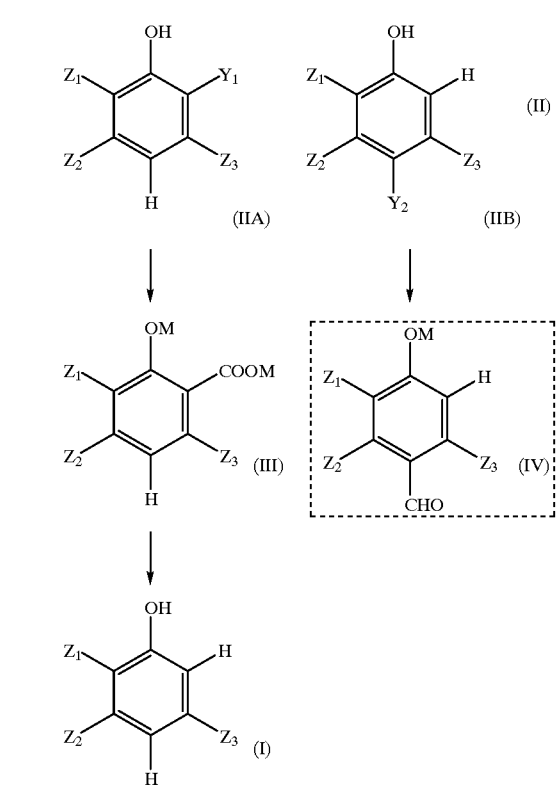

where, in said formulae (I) to (IV):

$Y_1$, and $Y_2$, which may be identical or different, represent one of the following groups:
a —CHO group,
a —CH$_2$OH group,
M represents a hydrogen atom and/or a metal cation from group (Ia) or (IIa) of the periodic classification, or an ammonium cation,
$Z_1$, $Z_2$ and $Z_3$ have the meanings given above.

In the present text, references are made hereinafter to the periodic classification of the elements as published in the "Bulletin de la Societe Chirnique de France", no. 1 (1966).

In accordance with the process of the invention, the $Y_1$ group in position 2 of a phenolic compound (A) having preferably the formula (IIA), is selectively oxidized to a carboxy group, and optionally a hydroxymethyl group in the 4 position of a phenolic compound (B) preferably having the formula (IIB), is selectively oxidized to a formyl group.

Oxidation is effected by molecular oxygen or a gas containing molecular oxygen, generally in the presence of a catalyst.

A preferred oxidation method consists of oxidising a mixture of phenolic compounds having the formula (II) in the liquid phase using molecular oxygen or a gas containing molecular oxygen, in an aqueous medium comprising a basic agent, in the presence of a catalyst based on a metal $M_1$ selected from metals from group 1b and 8 of the periodic classification of the elements, optionally comprising as an activator metals such as cadmium, cerium, bismuth, lead, silver, tellurium or tin.

According to the invention, it was discovered in a totally unexpected manner that if the temperature was increased and the reaction was preferably carried out under pressure, or if the quantity of the base present during oxidation was increased, the formyl and/or hydroxymethyl groups in the 2 position of molecule (A) were selectively oxidized to a carboxy group, and the group in the 4 position of molecule (B) was at the most oxidized to a formyl group.

The catalysts used in the process of the invention are based on a metal from the group 1b and 8 of the periodic classification.

Examples of catalysts based on a metal from group 8 of the periodic classification are nickel, ruthenium, rhodium, palladium, osmium, iridium, platinum and mixtures thereof. Of the metals from group 1b, copper is preferred.

Preferably, platinum and/or palladium catalysts are used, taken from all the available forms such as, for example: platinum black, palladium black, platinum oxide, palladium oxide, or the noble metal itself, deposited on different supports such as carbon black, calcium carbonate, activated aluminas and silicas, or equivalent materials. Catalytic masses based on carbon black are particularly suitable.

The quantity of catalyst to be used, expressed as the weight of metal $M_1$ with respect to that of the mixture of phenolic compounds with formula (II) can vary from 0.01 to 10%, and preferably 0.04 to 2%.

Further details of the catalysts can be obtained from U.S. Pat. No. 3,673,257, FR-A-2 305 420 and FR-A-2 350 323.

An activator is preferably used in the catalysts employed in the process of the invention.

The activator can be selected from all those mentioned in the above patents. Bismuth, lead and cadmium, in the form of the free metal or as cations, are preferably used. In the latter case, the associated anion is not critical and all derivatives of these metals can be used. Preferably, bismuth metal or derivatives thereof is used.

An inorganic or organic bismuth derivative of bismuth can be used, in which the bismuth atom has an oxidation number greater than zero, for example 2, 3, 4 or 5. The residue associated with the bismuth is not critical once it satisfies this condition. The activator can be soluble or insoluble in the reaction medium.

Illustrative compounds of activators which can be used in the process according to the present invention are: bismuth oxides; bismuth hydroxides; salts of inorganic hydracids such as: bismuth chloride, bromide, iodide, sulphide, selenide or telluride; salts of inorganic oxyacids such as: bismuth sulphite, sulphate, nitrite, nitrate, phosphite, phosphate, pyrophosphate, carbonate, perchlorate, antimonate, arsenate, selenite or selenate; and salts of oxyacids derived from transition metals such as: bismuth vanadate, niobate, tantalate, chromate, molybdate, tungstate or permanganate.

Other suitable compounds are the salts of aliphatic or aromatic organic acids such as: bismuth acetate, propionate, benzoate, salicylate, oxalate, tartrate, lactate, or citrate; and phenates such as: bismuth gallate or pyrogallate. These salts and phenates can also be bismuthyl salts.

Other inorganic or organic compounds which can be used are binary compounds of bismuth with elements such as phosphorous or arsenic; heteropolyacids containing bismuth and salts thereof; and aliphatic and aromatic bismuthines are also suitable.

Specific examples are:
oxides: BiO; $Bi_2O_3$; $Bi_2O_4$; $Bi_2O_5$,
hydroxides: $Bi(OH)_3$,
salts of inorganic hydracids: bismuth chloride $BiCl_3$; bismuth bromide
$BiBr_3$; bismuth iodide $BiI_3$; bismuth sulphide $Bi_2S_3$; bismuth selenide $Bi_2Se_3$; bismuth telluride $Bi_2Te_3$,
salts of inorganic oxyacids: basic bismuth sulphite $Bi_2(SO_3)_3,Bi_2O_3,5H_2O$; neutral bismuth sulphate $Bi_2(SO_4)_3$; bismuthyl sulphate $(BiO)HSO_4$; bismuthyl nitrite $(BiO)NO_2,0.5H_2O$; neutral bismuth nitrate $Bi(NO_3)_3,5H_2O$; double nitrate of bismuth and magnesium $2Bi(NO_3)_3,3Mg(NO_3)_2,24H_2O$; bismuthyl nitrate $(BiO)NO_3$; bismuth phosphite $(Bi_2(PO_3H)_3, 3H_2O$; neutral bismuth phosphate $BiPO_4$; bismuth pyrophosphate $Bi_4(P_2O_7)_3$; bismuthyl carbonate $(BiO)_2 CO_3,0.5H_2O$; neutral bismuth perchlorate $Bi(ClO_4)_3,5H_2O$; bismuthyl perchlorate $(BiO)ClO_4$; bismuth antimonate $BiSbO_4$; neutral bismuth arsenate $Bi(AsO_4)_3$; bismuthyl arsenate $(BiO)AsO_4,5H_2O$; bismuth selenite $Bi_2(SeO_3)_3$,
salts of oxyacids derived from transition metals: bismuth vanadate $BiVO_4$; bismuth niobate $BiNbO_4$; bismuth tantalate $BiTaO_4$; neutral bismuth chromate $Bi_2(CrO_4)$; bismuthyl dichromate $[(BiO)_2]Cr_2O_7$; acid bismuthyl chromate $H(BiO)CrO_4$; double chromate of bismuthyl and potassium $K(BiO)CrO_4$; bismuth molybdate $Bi_2(MoO_4)_3$; bismuth tungstate $Bi_2(WO_4)_3$; double molybdate of bismuth and sodium $NaBi(MoO_4)_2$; basic bismuth permanganate $Bi_2O_2(OH)MnO_4$,
salts of aliphatic or aromatic organic acids: bismuth acetate $Bi(C_2H_3O_2)_3$; bismuthyl propionate $(BiO)C_3H_5O_2$; basic bismuth benzoate $C_6H_5CO_2Bi(OH)_2$;

bismuthyl salicylate $C_6H_4CO_2(BiO)(OH)$; bismuth oxalate $(C_2O_4)_3Bi_2$; bismuth tartrate $Bi_2(C_4H_4O_6)_3$, $6H_2O$; bismuth $(C_6H_9O_5)OBi,7H_2O$; bismuth citrate $C_6H_5O_7Bi$, phenates: basic bismuth gallate $C_7H_7O_7Bi$; basic bismuth pyrogallate $C_6H_3(OH)_2(OBi)(OH)$.

Other suitable inorganic or organic compounds are: bismuth phosphide BiP; bismuth arsenide $Bi_3As_4$; sodium bismuthate $NaBiO_3$; bismuth-thiocyanic acids $H_2[Bi(BNS)_5]$, $H_3[Bi(CNS)_6]$ and sodium and potassium salts thereof; trimethylbismuthine $Bi(CH_3)_3$, triphenylbismuthine $Bi(C_6H_5)_3$.

The bismuth derivatives which are preferably used in the process according to the invention are: bismuth oxides; bismuth hydroxides; bismuth or bismuthyl salts of inorganic hydracids; bismuth or bismuthyl salts of inorganic oxyacids; bismuth or bismuthyl salts of aliphatic or aromatic organic acids; and bismuth or bismuthyl phenates.

A particularly suitable group of activators for implementing the process of the invention is constituted by: bismuth oxides $Bi_2O_3$ and $Bi_2O_4$; bismuth hydroxide $Bi(OH)_3$; neutral bismuth sulphate $Bi_2(SO_4)_3$; bismuth chloride $BiCl_3$; bismuth bromide $BiBr_3$; bismuth iodide $BiI_3$; neutral bismuth nitrate $Bi(NO_3)_3,5H_2O$; bismuthyl nitrate $BiO(NO_3)$; bismuthyl carbonate $(BiO)_2CO_3,0.5H_2O)$; bismuth acetate $Bi(C_2H_3O_2)_3$; and bismuthyl salicylate $C_6H_4CO_2(BiO)(OH)$.

The quantity of activator used, expressed as the quantity of metal contained in the activator with respect to the weight of metal $M_1$ used, can vary between wide limits. For example, this quantity can be as little at 0.1% and can reach the weight of metal $M_1$ used, or even exceed it without any problems.

More particularly, this quantity is selected so that it provides the oxidation medium with 10 to 900 ppm by weight of activator metal with respect to the mixture of phenolic compounds having the formula (II). In this respect, higher quantities of activator, of the order of 900 to 1500 ppm, can naturally be used, but with no significant additional advantage.

According to the process of the invention, oxidation is carried out in an aqueous medium containing a basic agent in solution, and more particularly ammonium hydroxide, alkaline or alkaline-earth bases, for example hydroxides such as sodium, potassium, lithium and barite hydroxide; alkaline alkanolates such as sodium or potassium methylate, ethylate, isopropylate and tert-butylate, sodium or potassium carbonates or bicarbonates, and in general, the salts of alkaline or alkaline-earth bases and weak acids.

Thus, the compounds with formula (III) and (IV) can be completely or partially turned into salts depending on the quantity of basic agent used. It follows that in said formulae, M symbolises a hydrogen atom and/or a metal cation from group (Ia) or (IIa), or an ammonium cation.

Sodium or potassium hydroxide is used for reasons of economy. The proportion of inorganic base to be used can be between 0.5 to 10 moles, preferably between 1 and 4 moles, and still more preferably between 2 and 4 moles of inorganic base per mole of phenolic compounds with formula (II).

The concentration by weight of the mixture of phenolic compounds with formula (II) in the liquid phase is usually between 1% and 60%, preferably between 2% and 30%.

In practice, one manner of implementing the process consists of bringing the solution comprising the mixture of phenolic compounds with formula (II), the basic agent, the catalyst based on metal Ml, and any activator, into contact with molecular oxygen or a gas containing molecular oxygen, for example air, in the proportions indicated above.

Atmospheric pressure can be used, but it is preferable to work under a pressure of between 1 and 20 bar.

The mixture is then stirred at the desired temperature until a quantity of oxygen corresponding to that necessary for transforming the hydroxymethyl or formyl group of the compound (A) into a carboxy group, and optionally the hydroxymethyl group of the compound (B) into a formyl group, has been consumed.

The temperature of the reaction to be used varies according to the thermnal stability of the products to be prepared.

In accordance with the invention, the temperature is preferably selected in a temperature range going from 30° C. to 200° C., preferably between 40° C. and 160° C.

The skilled person will adapt the temperature according to the reaction conditions (in particular the quantity of base, nature of the metal $M_1$, pressure and stirring). It has been found, in particular, that the lower the temperature, the greater the quantity of basic agent which must be used.

By way of examples, the preferred conditions for the preferred metals, platinum and palladium, will be given. For platinum, as the temperature selected is between 100° C. and 160° C., the quantity of base to be used is advantageously between 1 and 3 moles per mole of phenolic compounds with formula (II). In the case of palladium, the temperature can be selected between 30° C. and 200° C., preferably between 30° C. and 150° C., and for this latter range, the quantity of base is preferably 2 to 4 moles per mole of phenolic compounds.

Thus, the quantity of base has to be sufficient to oxidise the Y1 group, in the ortho position, to a carboxy group. It is determined by the skilled person according to the temperature and the metal selected.

At the end of the reaction, which preferably lasts between 30 minutes and 6 hours, 2-hydroxybenzoic acid which can be partially or totally in its salt form, and preferably has formula (III), and a 4-hydroxybenzaldehyde preferably having formula (IV), can be recovered.

After any necessary cooling, the catalytic mass is then separated from the reaction medium, for example by filtration.

4-hydroxybenzaldehyde will be recovered from the reaction medium.

A first method for treatment of the reaction medium consists of pH controlled extraction of the 4-hydroxybenzaldehyde.

To this end, the reaction medium is placed in contact with an organic solvent able to extract aldehyde.

A solvent is chosen which is non-miscible with water.

Examples of solvents suitable for the invention are, in particular, ketones such as methylethylketone, methylisobutylketone, cylcohexanone; esters such as ethyl acetate, isopropyl acetate, butyl acetate; ether oxides such as diethylether, diisopropylether, methyl-tert-butylether, ethyl-tert-butylether, di-n-butylether; heavy alcohols (containing preferably at least 4 atoms of carbon) such as butanol, hexanol, octanol, cyclohexanol; aliphatic hydrocarbons such as n-pentane, hexane, heptane and cyclohexane; halogenated aliphatic hydrocarbons such as dichloromethane, dichloroethane; aromatic hydrocarbons such as toluene, xylenes; halogenated aromatic hydrocarbons such as monochlorobenzene, dichlorobenzene, and mixtures thereof.

The reaction medium is thus placed in contact with the reaction solvent, generally at one volume of solvent per volume of medium.

1 or more extractions can be carried out, for example 5, and more preferably 1 to 3.

Prior, or at the same time as the addition of the solvent, the pH is returned to between 4 and 9 by adding a protonic acid of inorganic origin, preferably hydrochloric acid or sulphuric acid such as, for example, trifluoromethanesulphonic acid or methanesulphonic acid. The concentration of the acid is immaterial and commercially available forms are preferably used.

The aqueous and organic phases are separated.

The aqueous phase comprises 2-hydroxybenzoic acid in salt form.

The organic phase comprises 4-hydroxybenzaldehyde which is perhaps then recovered according to conventional techniques, particularly by distillation.

The aqueous phase can be treated by carrying out decarboxylation of the 2-hydroxybenzoic acid obtained, the description of which is set out in detail in the second variation, which allows regeneration of the starting phenolic compound which can then be recycled.

According to a second variation of the process of the invention, at the end of the reaction producing 2-hydroxybenzoic acid partially or completely in its salt form and 4-hydroxybenzaldehyde, a decarboxylation reaction is carried out on the reaction medium.

This is effected by acidifying the resulting medium by adding a protonic acid of inorganic origin, particularly those previously described, until a pH of less than or equal to 3 is obtained.

The reaction medium is heated to a temperature varying, for example, between 120° C. and 350° C., and preferably between 150° C. and 220° C.

The process is preferably carried out under the autogenous pressure of the reactants.

At the end of the reaction, the reaction medium is cooled between 20° C. and 80° C.

A two-phase medium is obtained, constituted by an organic phase comprising on the one hand 4-hydroxybenzaldehyde, preferably with formula (IV) and the starting phenolic compound with formula (I), and on the other hand a saline aqueous phase.

The organic and aqueous phases are separated and the 4-hydroxybenzaldehyde is recovered from the organic phase using conventional separation techniques, for example by extraction using a suitable solvent and then by distillation. Reference may be made to the description of the first variation.

In accordance with the process of the invention, the mixture used is of two phenolic compounds, one carrying a formyl or hydroxymethyl group in the 2 position, and the other carrying a formyl or hydroxymethyl group in the 4 position.

The starting compounds (IIA) and (IIB) therefore have more particularly the following formulae:

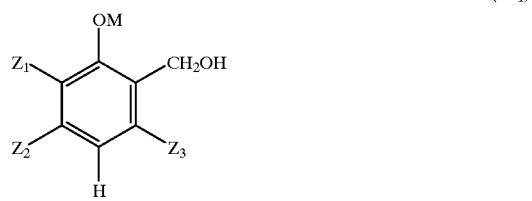

(IIa$_1$)

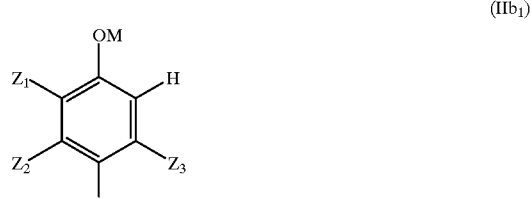

(IIb$_1$)

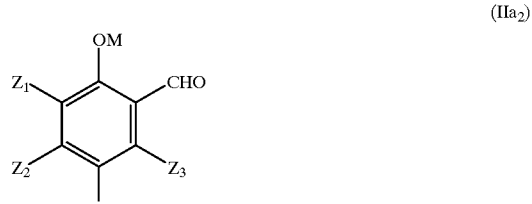

(IIa$_2$)

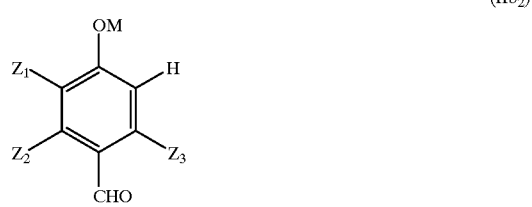

(IIb$_2$)

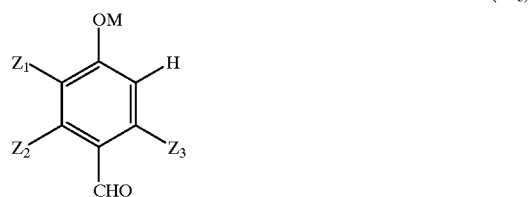

(IIa$_3$)

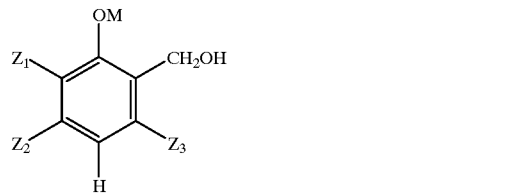

(IIb$_3$)

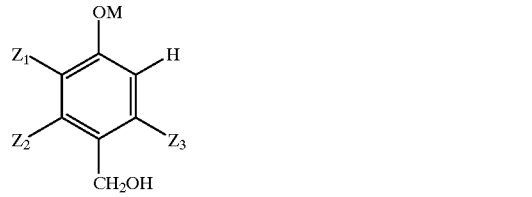

(IIa$_4$)

-continued

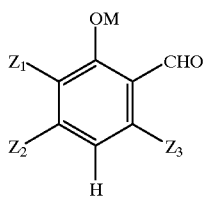

(IIb₄)

in said formulae, $M_1$, $Z_1$, $Z_2$ and $Z_3$ have the meanings previously described.

The mixtures of phenolic compounds to which the process according to the invention can be applied are generally known products which can be prepared by various methods of organic synthesis.

Thus, mixtures with formula (IIa₁) and (IIb₁) can be obtained by a process of hydroxymethylation of a phenol by condensation thereof with formaldehyde or a formaldehyde generator in an aqueous phase in the presence of an alkaline or alkaline-earth base.

More precisely, there is an unsubstituted phenol on the ortho and para positions with respect to the hydroxy group, with the general formula (I):

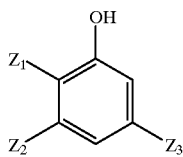

(I)

in which $Z_1$, $Z_2$ and $Z_3$ have the meanings previously described.

Examples of phenols with formula (I) which may act as a starting point for the synthesis of compounds with formula (II) are phenol, pyrocatechin, guaiacol, guetol, 3-methoxyphenol, 3-ethoxyphenol, 3-isopropoxyphenol, 3-t-butoxyphenol, m-cresol and o-cresol.

The conditions selected for this hydroxymethylation step are those taught by the prior art listed hereinafter: see in particular H. G. PEER, Rec. Trav. Chim. Pays-Bas [Netherlands] 79 825–835 (1960); GB-A-774 696; GB-A-751 845; EP-A-165; J. H. FREEMAN, J. Am. Chem. Soc. 74 6 257–6 260 (1952) and 76 2080–2087 (1954); H. G. PEER, Rec. Trav. Chim. Pays-Bas [Netherlands] 78 851–863 (1959); H. EULER et al Arkiv für Chem. 13 1–7 (1939); P. CLAUS et al Monath. Chem. 103 1178–11293 (1972).

Formaldehyde or any formaldehyde generator can be used such as, for example, trioxane or paraformaldehyde used as linear paraformaldehydes of any degree of polymerisation, preferably containing 8 to 100 ($CH_2O$) units.

Formaldehyde can be used in the form of an aqueous solution of non-critical concentration. It can vary between 20 and 50% by weight; preferably commercial solutions are used which have a concentration of about 30 to 40% by weight.

The quantity of formaldehyde expressed as moles of formaldehyde per mole of phenol can vary between wide limits. The formaldehyde/phenol molar ratio can vary between 0.5 and 2.0, and preferably between 0.5 and 1.5.

The quantity of base present in the hydroxymethylation medium, expressed as the number of moles of base/phenolic hydroxy group of the phenol to be hydroxymethylated, can vary between broad limits. In general, this ratio, which is variable depending on the nature of the base, can vary between 0.1 and 2, and preferably between 0.5 and 1.1. The base used can be one of those cited above for the oxidation phase. The use of alkaline hydroxides in aqueous solution is particularly convenient.

In general, the hydroxymethylation step is carried out at a temperature between 0 and 100° C., preferably between 20 and 70° C.

The process is preferably carried out under the pressure which is autogenous for the reactants to avoid any possible losses of paraformaldehyde, which may be gaseous at the temperatures used.

Preferably, the reaction is carried out under a controlled atmosphere of inert gases such as nitrogen or noble gases, for example argon.

The reaction time can be very variable. It is usually between 30 minutes and 24 hours, preferably between 4 hours and 8 hours.

In practice, the reaction is readily carried out by placing the phenol and formaldehyde, and any base, in the equipment, then stirring and heating the reaction mixture to the temperature desired for the time required to complete the reaction.

The order of introduction of the reactants is not critical and can thus be different.

A mixture of phenolic compounds with formula (Ia₁) and (IIb₁) is obtained.

The compounds with formula (IIa₂) and (IIb₂) can be prepared by oxidation of hydroxymethylated phenolic compounds with formula (IIa₁) and (IIb₁), by oxidation with molecular oxygen or a gas containing molecular oxygen, in an alkaline aqueous phase in the presence of a catalyst based on a metal from group 8 of the periodic classification, preferably platinum and palladium, optionally containing metals such as cadmium, cerium, bismuth, lead, silver, tellurium or tin as an activator. Such processes have been described in U.S. Pat. No. 3,673,257, FR-A-2 305 420, and in FR-A-2 350 323.

If necessary, the pH of the solution is brought to a value between 8 and 13 by optional addition of an alkaline or earth-alkaline base. The optimum pH value depends on the nature of the hydroxymethylated phenols.

For example, in the case of a platinum catalyst, the quantity of base to be used is advantageously between 1 and 3 moles per mole of hydroxymethylated phenolic compounds, and between 0.5 and 2 in the case of a paliadium catalyst.

The temperature of the oxidation reaction is between 10° C. and 60° C., and preferably between 20° C. and 50° C.

More specifically again, the process according to the present invention is very suitable for the preparation of compounds with formula (IIa₂) and (IIb₂) from phenolic compounds with formula (IIa₁) and (IIb₁) resulting from the first step, by molecular oxygen or a gas containing molecular gas in the presence of a catalyst based on a metal from group 8 of the periodic classification, optionally containing a metal such as those used as an activator, without intermediate separation of the hydroxymethylated phenolic compounds.

It appears particularly advantageous for industry to implement the process according to the present invention using compounds with formula (IIa$_2$) and (IIb$_2$) obtained by a two-step process comprising:

hydroxymethylation of a phenol in an aqueous medium in the presence of an alkaline or earth-alkaline base, by formaldehyde or a formaldehyde generator, producing a mixture of hydroxymethylated phenolic compounds, one hydroxymethylated in the 2 position, the other in the 4 position, and oxidation, without intermediate separation, of phenolic compounds obtained by molecular oxygen or a gas containing molecular oxygen in an alkaline aqueous phase in the presence of a catalyst based on a metal from group 8 of the periodic classification, with optionally as an activator, a metal such as those previously listed.

A supplementary importance of the process of the invention is that it allows the use of mixtures of phenolic compounds directly produced from the preceding steps of hydroxymethylation and optionally of oxidation.

As previously mentioned, the process of the invention is particularly suitable for the preparation of vanillin and of ethylvanillin from a mixture of phenolic compounds obtained by hydroxymethylation of guaiacol or of guetol.

Thus, vanillin can be prepared by selective oxidation of the hydroxymethyl group in the 2 position of compound (A) of a mixture of phenolic compounds, o-hydroxymethylguaiacol (A) and p-hydroxymethylguaiacol (B), to the carboxy group, and of the hydroxymethyl group of compound (B) in the 4 position to the formyl group, thus producing a mixture of a 2-hydroxy-3-methoxybenzoic acid and vanillin, then of recovering the latter.

Another variation consists of selective oxidation of the formyl group in the 2 position of compound (A) of a mixture of phenolic compounds, o-formylguaiacol (A) and p-formylguaiacol (B), to the carboxy group, thus producing a mixture of a 2-hydroxy-3-methoxybenzoic acid and vanillin, then of recovering the latter.

With regard to the preparation of ethylvanillin, in accordance with the invention, the hydroxymethyl group in the 2 position of compound (A) of a mixture of phenolic compounds, o-hydroxymethylguaiacol (A) and p-hydroxymethylguaiacol (B) is selectively oxidised to the carboxy group, and the hydroxymethyl group of compound (B) in the 4 position to the formyl group, thus producing a mixture of a 2-hydroxy-3-ethoxybenzoic acid and ethylvanillin, then of recovering the latter.

Another variation is in the fact that in a mixture of phenolic compounds, o-formylguetol (A) and p-formylguetol (B), there is selective oxidation of the formyl group in the 2 position of compound (A) to the carboxy group, thus producing a mixture of a 2-hydroxy-3-ethoxybenzoic acid and ethylvanillin, then of recovering the latter.

Examples of implementations of the invention will be given below. These examples are given by way of illustration are in no way limiting.

In the examples, the degree of conversion and the yield obtained is defined.

The degree of conversion (DC) corresponds to the ratio between the number of moles of substrate transformed and the number of moles of substrate used.

The yield (YY) corresponds to the ratio between the number of moles of product formed and the number of moles of substrate used.

The yield (YT$_{vanillin}$) corresponds to the ratio between the number of moles of vanillin formed and the number of moles of guaiacol transformed in the sequence.

In the examples, the abbreviations are:

o-hydroxymethylguaiacol=OMG
p-hydroxymethylguaiacol=PMG
o-vanillin=3-methoxy-2-hydroxybenzaldehyde=OVA
p-vanillin=3-methoxy-4-hydroxybenzaldehyde=PVA
o-vanillic acid=2-hydroxy-3-methylbenzoic acid=AOV
p-vanillic acid=4-hydroxy-3-methylbenzoic acid=APV

EXAMPLES

Example 1

In this example, a mixture of o-hydroxymethylguaiacol and p-hydroxymethylguaiacol is oxidised.

2700 g of an aqueous solution containing 28.5 g of o-hydroxymethylguaiacol (OMG) and 33.72 g of p-hydroxymethylguaiacol (PMG) and 148 g of sodium carbonate is introduced into a pressurised 3.9l autoclave provided with an automatic exhaust turbine.

This aqueous solution is the product of condensation of guaiacol on formol in an aqueous base solution, and prepared as described in the prior art (particularly according to example 4 in U.S. Pat. No. 4,351,962).

0.54 g of bismuth trioxide and 22 g of palladium catalyst, deposited on charcoal in an amount of 3% by weight of metal, is added to this reaction mixture.

The reaction mixture is stirred at 1500 rpm and the temperature thereof increased to 45° C. in nitrogen.

A pressure of 3 bar is established and air introduced into the reaction medium at a rate of 300 g/h.

The reaction mixture is kept under these conditions for 6 hours.

The reaction mixture is cooled and the pressure returned to atmospheric pressure, then the catalyst is filtered.

The reaction medium is then analysed using high performance liquid chromatography.

The results obtained are as follows:
DC OMG=100%
YY o-vanillin 7%
YY o-vanillic=93%
DC PMG=100%
YY p-vanillin=89%
YY p-vanillic acid=7%

Examination of these results shows that o-vanillin was selectively oxidised, compared to p-vanillin.

Example 2

In this example, a mixture of o-vanillin/p-vanillin is oxidised.

50.26 g of o-vanillin, 49.88 g of p-vanillin, 2003 g of water and 142.5 g of an aqueous solution of 30% by weight of sodium carbonate is introduced into a 3.9l autoclave provided with an automatic exhaust turbine.

22 g of palladium catalyst, deposited on charcoal in an amount of 3% by weight of metal, and 0.96 g of bismuth trioxide is added to the reaction mixture.

The mixture is stirred at 1500 rpm and the temperature thereof is increased to 140° C. in nitrogen.

A pressure of 13 bar is established and air introduced at a rate of 300 g/h for 15 minutes.

The reaction mixture is cooled and the pressure returned to atmospheric pressure, then the catalyst is filtered.

The reaction medium is then analysed using high performance liquid chromatography.

The results obtained are as follows:
DC o-vanillin=100%
YY o-vanillic acid=90%
DC p-vanillin=20%
YY p-vanillic acid=16%

This clearly demonstrates the selectivity of the oxidation.

Example 3

Example 2 is repeated, but using a platinum catalyst.

50.5 g of o-vanillin, 50.1 g of p-vanillin, 2003 g of water and 142.5 g of an aqueous solution of 30% by weight of sodium carbonate is introduced into a 3.91 autoclave provided with an automatic exhaust turbine.

22 g of platinum catalyst, deposited on charcoal in an amount of 5% by weight of metal, and 1.5 g of bismuth trioxide is added to this reaction mixture.

The mixture is stirred at 1500 rpm and the temperature thereof increased to 140° C. in nitrogen.

A pressure of 13 bar is established and air introduced at a rate of 300 g/h for 30 minutes.

The reaction mixture is cooled and the pressure returned to atmospheric pressure, then the catalyst is filtered.

The reaction medium is then analysed using high performance liquid chromatography.

The results obtained are as follows:
DC o-vanillin 100%
YY o-vanillic acid 89%
DC p-vanillin=15%
YY p-vanillic acid=12%

This also clearly demonstrates the selectivity of the oxidation.

What is claimed is:

1. A process for the preparation of a 2-hydroxybenzoic acid and a 4-hydroxybenzaldehyde and derivatives thereof, comprising the steps of:

a) mixing a starting phenolic compound carrying a formyl or hydroxymethyl group in the 2 position, and a starting phenolic compound carrying a formyl or hydroxymethyl group in the 4 position, b) selectively oxidizing the formyl or hydroxymethyl group in the 2 position of the phenolic compound carrying said group to a carboxy group, c) optionally, selectively oxidizing the hydroxymethyl group in the 4 position of the phenolic compound carrying said group to a formyl group, and d) recovering a mixture of 2-hydroxybenzoic acid and 4-hydroxybenzaldehyde and derivatives thereof.

2. A process according to claim 1, wherein the mixture of phenolic compounds has general formula (II):

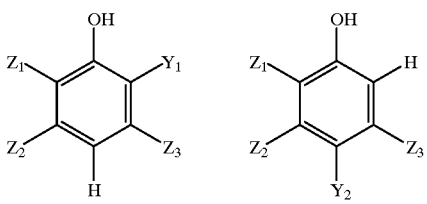

wherein:
Y1 and Y2, which may be identical or different, is a —CHO or a —CH$_2$OH group, $Z_1$, $Z_2$ and $Z_3$, which may be identical or different, represent a hydrogen atom, an alkyl, alkenyl, alkoxy, hydroxyalkyl, alkoxyalkyl, cycloalkyl, aryl, hydroxy, nitro, trifluoromethyl group or a halogen atom.

3. A process according to claim 2, wherein the phenolic compounds have formula (IIA) and (IIB), wherein $Z_1$, $Z_2$ and $Z_3$, which are identical or different, represent a hydrogen atom, a linear alkyl radical containing 1 to 12 carbon atoms, a branched alkyl radical containing 1 to 12 carbon atoms, a linear alkenyl radical containing 2 to 12 carbon atoms, a branched alkenyl radical containing 2 to 12 carbon atoms, a linear alkoxy radical containing 1 to 12 carbon atoms, a branched alkoxy radical containing 1 to 12 carbon atoms, a phenyl radical, or a halogen atom.

4. A process according to claim 3, wherein $Z_1$ represents a hydrogen atom, a linear alkoxy group containing 1 to 6 carbon atoms, or a branched alkoxy group containing 1 to 6 carbon atoms, $Z_2$ and $Z_3$ represent a hydrogen atom;

and $Y_1$ and $Y_2$ are identical and represent a formyl group or a hydroxymethyl group.

5. A process according to claim 2, wherein the mixture of phenolic compounds having formula (II) is:

o-hydroxymethylphenol and p-hydroxymethylphenol,
o-hydroxymethylguaiacol and p-hydroxymethylguaiacol,
o-formylguaiacol and p-formylguaiacol,
o-hydroxymethylguetol and p-hydroxymethylguetol, or
o-formylguetol and p-formylguetol.

6. A process according to claim 2, wherein in step b) and c), the mixture of phenolic compounds having the formula (II) is oxidized using molecular oxygen or a gas containing molecular oxygen, in an aqueous medium comprising a basic agent, in the presence of a catalyst comprising a metal $M_1$ selected from the group consisting of metals from group 1b and 8 of the periodic classification of the elements.

7. A process according to claim 6, wherein said aqueous medium further comprises, as an activator, a metal selected from the group consisting of cadmium, cerium, bismuth, lead, silver, tellurium and tin.

8. A process according to claim 6, wherein the catalyst is a metal selected from the group consisting of copper, nickel, ruthenium, rhodium, palladium, osmium, iridium, platinum and mixtures thereof.

9. A process according to claim 8, wherein the catalyst is platinum or palladium in the form of platinum black, palladium black, platinum oxide, palladium oxide, or the noble metal itself, deposited on a support.

10. A process according to claim 6, wherein the quantity of catalyst, expressed as the weight of metal $M_1$ with respect to that of the phenolic compounds of formula (II) is from 0.01 to 10%.

11. A process according to claim 7, wherein the activator is an inorganic or organic bismuth derivative selected from the group consisting of bismuth oxides, bismuth hydroxides, bismuth salts of inorganic hydracids, bismuthyl salts of inorganic hydracids, bismuth of inorganic oxyacids, bismuthyl salts of inorganic oxyacids, bismuth salts of aliphatic organic acids, bismuth salts of aromatic organic acids, bismuthyl salts of aliphatic organic acids, bismuthyl salts of aromatic organic acids, bismuth phenates, and bismuthyl phenates.

12. A process according to claim 11, wherein the bismuth derivative is selected from the group consisting of bismuth oxides $Bi_2O_3$ and $Bi_2O_4$, bismuth hydroxide $Bi(OH)_3$, bismuth chloride $BiCl_3$ bismuth bromide $BiBr_3$, bismuth iodide BiI3, neutral bismuth sulphate $Bi_2(SO_4)_3$, neutral bismuth nitrate $Bi(NO_3)_3,5H_2O$, bismuthyl nitrite $(BiO)NO_2$, $0.5H_2O$, bismuthyl carbonate $(BiO)_2CO_3,0.5H_2O$, bismuth acetate $Bi(C_2H_3O_2)_3$, and bismuthyl salicylate $C_6H_4CO_2(BiO)(OH)$.

13. A process according to claim 7, wherein the medium contains at least 0.1% by weight of metal activator with respect to the weight of metal $M_1$ used, and 10 to 900 ppm by weight of metal $M_1$ with respect to the phenolic compounds of formula (II).

14. A process according to claim 6, wherein the oxidation reaction is carried out within a temperature range of 30° C. to 200° C.

15. A process according to claim 6, wherein a pressure of 1 to 20 bar is used.

16. A process according to claim 6, wherein the oxidation is carried out in the aqueous medium containing, in solution, a basic agent, in a quantity such that it represents 0.5 to 10 moles, of inorganic base per mole of phenolic compounds of formula (II).

17. A process according to claim 16, wherein the temperature is between 30° C. and 200° C., and the basic agent is sodium or potassium hydroxyde.

18. A process according to claim 17, wherein the catalyst is platinum, the temperature is between 100° C. and 160° C.; the quantity of basic agent is between 1 and 3 moles per mole of phenolic compounds of formula (II).

19. A process according to claim 17, wherein the temperature is between 30° C. and 150° C.; the quantity of basic agent is between 2 and 4 moles per mole of phenolic compounds of formula (II).

20. A process according to claim 1, wherein step d) comprises the extraction in a solvent of 4-hydroxybenzaldehyde with controlled pH.

21. A process according to claim 20, wherein the solvent is selected from the group consisting of ketones, esters, ether oxides, heavy alcohols, aliphatic hydrocarbons, halogenated aliphatic hydrocarbons, aromatic hydrocarbons, and halogenated aromatic hydrocarbons.

22. A process according to claim 20, wherein the pH is returned to between 4 and 9 prior to the addition of the solvent or simultaneously by the addition of an inorganic protonic acid of inorganic origin to obtain an aqueous and organic phases, which are separated.

23. A process according to claim 1, further comprising the step of:

e) decarboxylating the 2-hydroxybenzoic acid, at least partially or completely in its salt form.

24. A process according to claim 23, wherein the 2-hydroxybenzoic acid has the general formula (III):

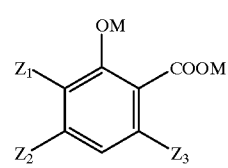

(III)

wherein:

M represents a hydrogen atom, a metal cation from group (Ia) or (IIa) or an ammonium cation, $Z_1$, $Z_2$, $Z_3$ which may be identical or different, represent a hydrogen atom, an alkyl, alkenyl, alkoxy, hydroxyalkyl, alkoxyalkyl, cycloalkyl, aryl, hydroxy, nitro, trifluoromethyl group or a halogen.

25. A process according to claim 23, wherein said step e) is carried out in a reaction medium comprising a protonic acid of mineral origin, at a pH less than or equal to 3.

26. A process according to claim 25, wherein the reaction medium is heated to a temperature between 120° C. and 350° C., and after cooling, the 4-hydroxybenzaldehyde is separated, which has the formula (IV):

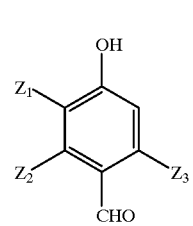

(IV)

wherein:

$Z_1$, $Z_2$, $Z_3$ which are identical or different, represent a hydrogen atom, an alkyl, alkenyl, alkoxy, hydroxyalkyl, alkoxyalkyl, cycloalkyl, aryl, hydroxy, nitro, trifluoromethyl group or a halogen atom.

27. A process according to claim 1, wherein the phenolic compounds have the formulae:

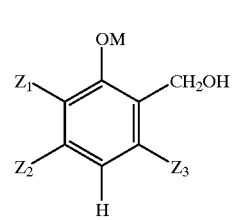

(IIa$_1$)

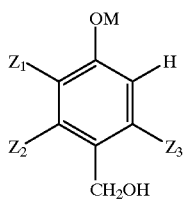 (IIb₁)

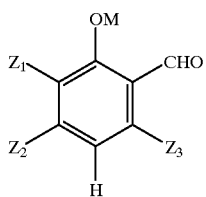 (IIa₂)

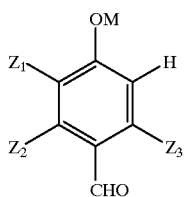 (IIb₂)

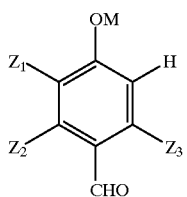 (IIa₃)

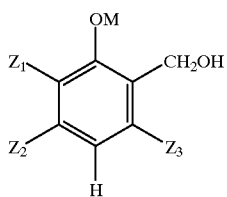 (IIb₃)

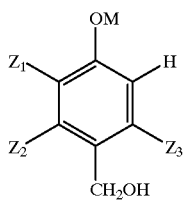 (IIa₄)

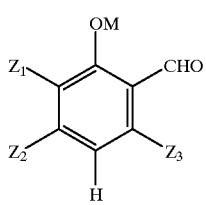 (IIb₄)

wherein:
M represents a hydrogen atom, a metal cation from group (Ia) or (IIa), or an ammonium cation,
$Z_1$, $Z_2$, $Z_3$ which may be identical or different, represent a hydrogen atom, an alkyl, alkenyl, alkoxy, hydroxyalkyl, alkoxyalkyl, cycloalkyl, aryl, hydroxy, nitro, trifluoromethyl group or a halogen atom.

28. A process according to claim 27, wherein the mixture of starting phenolic compounds is a mixture of compounds of formula (IIa₁) and (IIb₁) which is obtained by a reaction of hydroxymethylation of a phenol by condensation thereof with formaldehyde or a formaldehyde generator in an aqueous phase in the presence of an alkaline or earth alkaline base.

29. A process according to claim 28, wherein the starting phenol is an unsubstituted phenol at the ortho and para positions with respect to the hydroxy group, with the general formula (I):

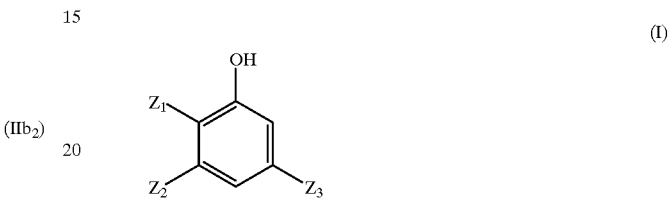 (I)

wherein $Z_1$, $Z_2$, $Z_3$ which are identical or different, represent a hydrogen atom, an alkyl, alkenyl, alkoxy, hydroxyalkyl, alkoxyalkyl, cycloalkyl, aryl, hydroxy, nitro, trifluoromethyl group or a halogen atom.

30. A process according to claim 29, wherein the phenol of formula (I) is phenol, pyrocatechin, guaiacol, guetol, 3-methoxyphenol, 3-ethoxyphenol, 3-isopropoxyphenol, 3-t-butoxyphenol, m-cresol or o-cresol.

31. A process according to claim 28, wherein the formaldehyde is trioxane or a paraformaldehyde containing 8 to 100 ($CH_2O$) units.

32. A process according to claim 28, wherein the formaldehyde/phenol molar ratio is between 0.5 and 2.0.

33. A process according to claim 28, wherein the quantity of base present in the hydroxymethylation medium, expressed as the number of moles of base/phenolic hydroxy group of the phenol to be hydroxymethylated, is between 0.1 and 2.

34. A process according to claim 28, wherein the temperature of the hydroxymethylation reacton is between 0 and 100° C.

35. A process according to claim 28, wherein the phenol, formaldehyde, and base, is placed in an equipment, and, then, while stirring, the reaction mixture is heated to the temperature desired for the time required to obtain a mixture of phenolic compounds with formulae (IIa₁) and (IIb₁).

36. A process according to claim 28, wherein a mixture of compounds of formulae (IIa₂) and (IIb₂) is obtained by oxidation of hydroxymethylated phenolic compounds of formulae (IIa₁) and (IIb₁), by oxidation using molecular oxygen or a gas containing molecular oxygen in an alkaline aqueous phase in the presence of a catalyst comprising a metal from group 8 of the periodic classification, optionally containing metals such as cadmium, cerium, bismuth, lead, silver, tellurium or tin as an activator.

37. A process according to claim 36, wherein the aqueous phase is brought to a ph of the value between 8 and 13 by optionally adding an alkaline or earth alkaline base.

38. A process according to claim 37, wherein the oxidation reaction is carried out at a temperature between 10° C. and 60° C.

39. A process according to claim 27, wherein a mixture of phenolic compounds of formulae (IIa$_2$) and IIb$_2$) is obtained by a two-step process comprising:

hydroxymethylation of a phenol in an aqueous medium in the presence of an alkaline or earth-alkaline base by formaldehyde or a formaldehyde generator producing a mixture of hydroxymethylated phenolic compounds, one hydroxymethylated in the 2 position, the other in the 4 position, and oxidation, without intermediate separation, of phenolic compounds obtained by molecular oxygen or a gas containing molecular oxygen in an alkaline aqueous phase in the presence of a catalyst comprising a metal from group 8 of the periodic classification, optionally as an activator.

40. A process for the preparation of vanillin according to claim 1, comprising the steps of:

a) mixing o-hydroxymethylguaiacol and p-hydroxymethylguaiacol, b) selectively oxidizing the hydroxymethyl group in the 2 position of o-hydroxymethylguaiacol to a carboxy group, c) selectively oxidising the hydroxymethyl group of p-hydroxymethylguaiacol to a formyl group, to produce a mixture of a 2-hydroxy-3-methoxybenzoic acid and vanillin, d) recovering a mixture of a 2-hydroxy-3-methoxybenzoic acid and vanillin, and, then, e) recovering vanillin from that mixture.

41. A process for the preparation of vanillin according to claim 1, comprising the steps of:

a) mixing o-formylguaiacol and p-formylguaiacol, b) selectively oxidizing the formyl group in the 2 position of o-formylguaiacol to a carboxy group, c) recovering a mixture of a 2-hydroxy-3-methoxybenzoic acid and vanillin, and, then, e) recovering vanillin from that mixture.

42. A process for the preparation of vanillin according to claim 1, comprising the steps of:

a) mixing o-hydroxymethylguetol and p-hydroxymethylguetol, b) selectively oxidising the hydroxymethyl group in the 2 position of o-hydroxymethylguetol to a carboxy group, c) selectively oxidising the hydroxymethyl group in the 4 position of p-hydroxymethylguetol to a formyl group, to produce a mixture of a 2-hydroxy-3-ethoxybenzoic acid and ethylvanillin, d) recovering a mixture of a 2-hydroxy-3-ethoxybenzoic acid and ethylvanillin, and, then, e) recovering ethylvanillin from that mixture.

43. A process for the preparation of vanillin according to claim 1, comprising the steps of:

a) mixing o-formylguetol and p-formylguaiacol, b) selectively oxidising the formyl group in the 2 position of o-formylguetol to a carboxy group, c) recovering a mixture of a 2-hydroxy-3-ethoxybenzoic acid and ethylvanillin, and, then, e) recovering ethylvanillin from that mixture.

\* \* \* \* \*